(12) United States Patent
Herold et al.

(10) Patent No.: US 7,132,569 B2
(45) Date of Patent: Nov. 7, 2006

(54) PREPARATION OF N-SUBSTITUTED 2,7-DIALKYL-4-HYDROXY-5-AMINO-8-ARYL-OCTANOYL AMIDES

(75) Inventors: Peter Herold, Basel (CH); Stefan Stutz, Basel (CH); Adriano Indolese, Möhlin (CH)

(73) Assignee: Speedel Pharma AG, Basel (CH)

( * ) Notice: Subject to any disclaimer, the term of this patent is extended or adjusted under 35 U.S.C. 154(b) by 0 days.

(21) Appl. No.: 11/254,749

(22) Filed: Oct. 21, 2005

(65) Prior Publication Data

US 2006/0041169 A1 Feb. 23, 2006

Related U.S. Application Data

(62) Division of application No. 10/048,229, filed as application No. PCT/CH00/00384 on Jul. 13, 2000.

(30) Foreign Application Priority Data

Jul. 29, 1999 (CH) .................................. 1401/99
Jan. 11, 2000 (CH) .................................. 0044/00

(51) Int. Cl.
*C07C 233/04* (2006.01)
*C07C 233/05* (2006.01)

(52) U.S. Cl. .................................................... 564/161
(58) Field of Classification Search ................. 564/161
See application file for complete search history.

(56) References Cited

FOREIGN PATENT DOCUMENTS

EP 0 678 503 10/1995

OTHER PUBLICATIONS

Herold, P., et al. "A Versatile and Stereocontrolled Synthesis of Hydroxyethylene Dipeptide Isosters", Journal of Organic Chemistry, vol. 54, No. 5 (Mar. 1989), pp. 1178-1185.
Cahiez, G., et al. "Highly Stereo- and Chemoselective Iron-Catalyzed Alkenylation of Organomagnesium Compounds", Synthesis, No. 8 (Aug. 1998), pp. 1199-1200.

*Primary Examiner*—Elvis O. Price
(74) *Attorney, Agent, or Firm*—Wenderoth, Lind & Ponack, L.L.P.

(57) ABSTRACT

From compounds of formula II

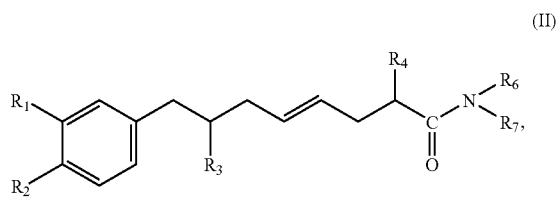

(II)

wherein $R_1$ and $R_2$ are independently of one another H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, and $R_5$ is $C_1$–$C_6$alkyl, $C_1$–$C_6$hydroxyalkyl, $C_1$–$C_6$alkoxy-$C_1$–$C_6$-alkyl, $C_1$–$C_6$alkanoyloxy-$C_1$–$C_6$alkyl, $C_1$–$C_6$aminoalkyl, $C_1$–$C_6$alkylamino-$C_1$–$C_6$-alkyl, $C_1$–$C_6$-dialkylamino-$C_1$–$C_6$-alkyl, $C_1$–$C_6$-alkanoylamido-$C_1$–$C_6$-alkyl, HO(O)C—$C_1$–$C_6$-alkyl, $C_1$–$C_6$alkyl-O—(O)C—$C_1$–$C_6$alkyl, $H_2N$—C(O)—$C_1$–$C_6$alkyl, $C_1$–$C_6$alkyl-HN—C(O)—$C_1$–$C_6$alkyl or ($C_1$–$C_6$alkyl)$_2$N—C(O)—$C_1$–$C_6$-alkyl, $R_6$ is $C_1$–$C_6$alkyl, $R_7$ is $C_1$–$C_6$alkyl or $C_1$–$C_6$alkoxy, or $R_6$ and $R_7$ together are tetramethylene, pentamethylene, 3-oxa-1,5-pentylene or —$CH_2CH_2O$— substituted, if necessary, with $C_1$–$C_4$-Alkyl, phenyl or benzyl, it is possible—through halolactonization, azidation of the halogen group, ring opening with an amine $R_5$—$NH_2$, and reduction of the azide group to form the amino group—to prepare compounds of formula I

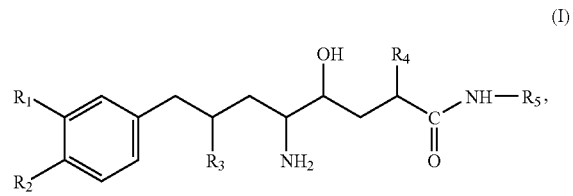

(I)

wherein $R_5$ is $C_1$–$C_6$alkyl, $C_1$–$C_6$hydroxyalkyl, $C_1$–$C_6$alkoxy-$C_1$–$C_6$alkyl, $C_1$–$C_6$alkanoyloxy-$C_1$–$C_6$alkyl, $C_1$–$C_6$aminoalkyl, $C_1$–$C_6$alkylamino-$C_1$–$C_6$alkyl, $C_1$–$C_6$dialkylamino-$C_1$–$C_6$-alkyl, $C_1$–$C_6$alkanoylamido-$C_1$–$C_6$alkyl, HO(O)C—$C_1$–$C_6$alkyl, $C_1$–$C_6$alkyl-O—(O)C—$C_1$–$C_6$alkyl, $H_2N$—C(O)—$C_1$–$C_6$alkyl, $C_1$–$C_6$alkyl-HN—C(O)—$C_1$–$C_6$alkyl or ($C_1$–$C_6$alkyl)$_2$—N—C(O)—$C_1$–$C_6$alkyl. If 2(S),7(R)-diastereomer of formula II is used, the 2(S),4(S),5(S),7(S)-diastereomer of formula Ia

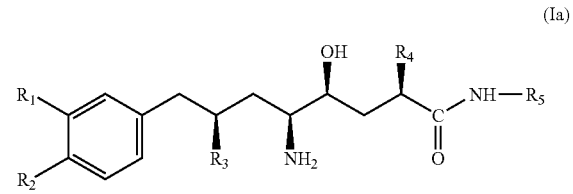

(Ia)

is obtained in a high degree of purity.

10 Claims, No Drawings

PREPARATION OF N-SUBSTITUTED 2,7-DIALKYL-4-HYDROXY-5-AMINO-8-ARYL-OCTANOYL AMIDES

This application is a Divisional application of Ser. No. 10/048,229, filed Jan. 29, 2002, which is a 371 application of PCT/CH00/00384 filed Jul. 13, 2000.

The invention relates to a process for the preparation of N-substituted 2,7-dialkyl-4-hydroxy-5-amino-8-aryl-octanoylamides and their physiologically acceptable salts; especially of N-(3-amino-2,2-dimethyl-3-oxopropyl)-2,7-di(1-methylethyl)-4-hydroxy-5-amino-8-[(4-methoxy-3-(3-methoxypropoxy)phenyl]octanamides and their physiologically acceptable salts, in particular of 2(S),4(S),5(S),7(S)-N-(3-amino-2,2-dimethyl-3-oxopropyl)-2,7-di(1-methylethyl)-4-hydroxy-5-amino-8-[4-methoxy-3-(3-methoxypropoxy)phenyl]octanamide and its physiologically acceptable salts; and new intermediate products used as intermediates in the multistage process.

In the EP-A-0 678 503, δ-amino-γ-hydroxy-ω-aryl-alkanecarboxamides are described, which exhibit renin-inhibiting properties and could be used as antihypertensive agents in pharmaceutical preparations. The manufacturing procedures described are unsatisfactory in terms of the number of process steps and yields and are not suitable for an industrial process. A disadvantage of these processes is also that the total obtainable yields of pure diastereomers are too small.

Surprisingly, it has now been found that these alkanecarboxamides are obtainable both in high total yields and in a high degree of purity, and that selective pure diastereomers are obtainable if the double bond of 2,7-dialkyl-8-aryl-4-octenoyl amides is simultaneously halogenated in the 5-position and hydroxylated in the 4-position under lactonization, replacing halogen with azide, amidating the lactone and then transferring the azide to the amine group.

A primary object of the invention is a process for the preparation of compounds of formula I,

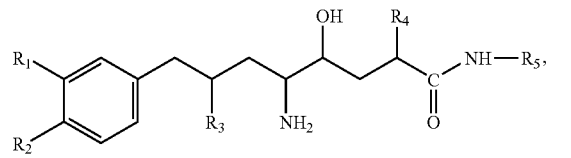

wherein
$R_1$ and $R_2$ are independently of one another H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, and $R_5$ is $C_1$–$C_6$alkyl, $C_1$–$C_6$hydroxyalkyl, $C_1$–$C_6$alkoxy-$C_1$–$C_6$alkyl, $C_1$–$C_6$alkanoyloxy-$C_1$–$C_6$alkyl, $C_1$–$C_6$aminoalkyl, $C_1$–$C_6$alkylamino-$C_1$–$C_6$-alkyl, $C_1$–$C_6$-dialkylamino-$C_1$–$C_6$-alkyl, $C_1$–$C_6$-alkanoylamido-$C_1$–$C_6$-alkyl, HO(O)C—$C_1$–$C_6$-alkyl, $C_1$–$C_6$alkyl-O—(O)C—$C_1$–$C_6$alkyl, $H_2N$—C(O)—$C_1$–$C_6$alkyl, $C_1$–$C_6$alkyl-HN—C(O)—$C_1$–$C_6$alkyl or $(C_1$–$C_{1-6}$alkyl)$_2$N—C(O)—$C_1$–$C_6$alkyl, comprising a) the reaction of a compound of formula II

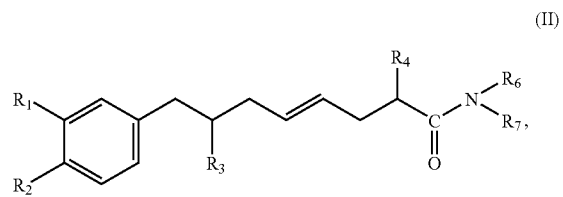

wherein
$R_6$ is $C_1$–$C_6$-alkyl, $R_7$ is $C_1$–$C_6$alkyl or $C_1$–$C_6$alkoxy, or $R_6$ and $R_7$ together are tetramethylene, pentamethylene, 3-oxa-1,5-pentylene or —CH$_2$CH$_2$O—C(O)— substituted if necessary with $C_1$–$C_4$alkyl, phenyl or benzyl, with a halogenation agent in the presence of water, and if necessary, an acid to form a compound of formula III,

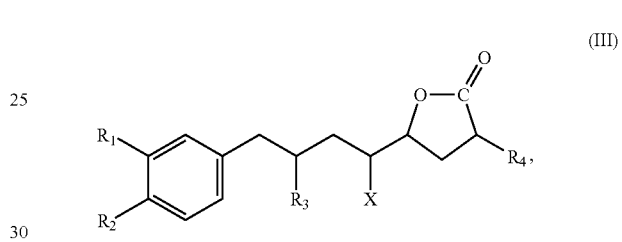

wherein X is Cl, Br or I, b) reaction of the compound of formula III with an azidation agent to form a compound of formula IV,

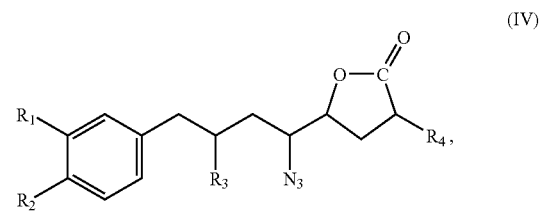

c) thereafter reaction of the compound of formula IV with an amine of formula $R_5$—NH$_2$ to form a compound of formula V,

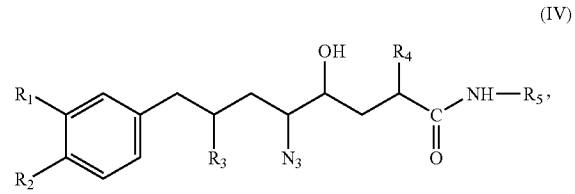

and d) for preparation of a compound of formula I, reduction of the azide group of the compound of formula V to form the amine group and then isolation of the compounds of formula I, if necessary with the addition of a salt-forming acid.

$R_1$ and $R_2$ may be linear or branched in the form of alkyl and preferably comprise 1 to 4 C-atoms. Examples are methyl, ethyl, n- and i-propyl, n-, i- and t-butyl, pentyl and hexyl.

$R_1$ and $R_2$ may be linear or branched in the form of halogenalkyl and preferably comprise 1 to 4 C-atoms, especially 1 or 2 C-atoms. Examples are fluoromethyl, difluoromethyl, trifluoromethyl, chloromethyl, dichloromethyl, trichloromethyl, 2-chloroethyl and 2,2,2-trifluoroethyl.

$R_1$ and $R_2$ may be linear or branched in the form of alkoxy and preferably comprise 1 to 4 C-atoms. Examples are methoxy, ethoxy, n- and i-propyloxy, n-, i- and t-butyloxy, pentyloxy and hexyloxy.

$R_1$ and $R_2$ may be linear or branched in the form of alkoxyalkyl. The alkoxy group preferably comprises 1 to 4 and especially 1 or 2 C-atoms, and the alkyl group preferably comprises 1 to 4 C-atoms. Examples are methoxymethyl, 1-methoxyeth-2-yl, 1-methoxyprop-3-yl, 1-methoxybut-4-yl, methoxypentyl, methoxyhexyl, ethoxymethyl, 1-ethoxyeth-2-yl, 1-ethoxyprop-3-yl, 1-ethoxybut-4-yl, ethoxypentyl, ethoxyhexyl, propyloxymethyl, butyloxymethyl, 1-propyloxyeth-2-yl and 1-butyloxyeth-2-yl.

$R_1$ and $R_2$ may be linear or branched in the form of $C_1$–$C_6$alkoxy-$C_1$–$C_6$alkyloxy. The alkoxy group preferably comprises 1 to 4 and especially 1 or 2 C-atoms, and the alkyoxy group preferably comprises 1 to 4 C-atoms. Examples are methoxymethyloxy, 1-methoxyeth-2-yloxy, 1-methoxyprop-3-yloxy, 1-methoxybut-4-yloxy, methoxypentyloxy, methoxyhexyloxy, ethoxymethyloxy, 1-ethoxyeth-2-yloxy, 1-ethoxyprop-3-yloxy, 1-ethoxybut-4-yloxy, ethoxypentyloxy, ethoxyhexyloxy, propyloxymethyloxy, butyloxymethyloxy, 1-propyloxyeth-2-yloxy and 1-butyloxyeth-2-yloxy.

In a preferred embodiment, $R_1$ is methoxy- or ethoxy-$C_1$–$C_4$alkyloxy, and $R_2$ is preferably methoxy or ethoxy. Particularly preferred are compounds of formula I, wherein $R_1$ is 1-methoxyprop-3-yloxy and $R_2$ is methoxy.

$R_3$ and $R_4$ may be linear or branched in the form of alkyl and preferably comprise 1 to 4 C-atoms. Examples are methyl, ethyl, n- and i-propyl, n-, i- and t-butyl, pentyl and hexyl. In a preferred embodiment, $R_3$ and $R_4$ in compounds of formula I are in case isopropyl.

$R_5$ may be linear or branched in the form of alkyl and preferably comprise 1 to 4 C-atoms. Examples of alkyl are listed hereinabove. Methyl, ethyl, n- and i-propyl, n-, i- and t-butyl are preferred.

$R_5$ may be linear or branched in the form of $C_1$–$C_6$hydroxyalkyl and preferably comprise 2 to 6 C-atoms. Some examples are 2-hydroxyethy-1-yl, 2-hydroxyprop-1-yl, 3-hydroxyprop-1-yl, 2-, 3- or 4-hydroxybut-1-yl, hydroxypentyl and hydroxyhexyl.

$R_5$ may be linear or branched in the form of $C_1$–$C_6$alkoxy-$C_1$–$C_6$alkyl. The alkoxy group preferably comprises 1 to 4 C-atoms and the alkyl group preferably 2 to 4 C-atoms. Some examples are 2-methoxyethy-1-yl, 2-methoxyprop-1-yl, 3-methoxyprop-1-yl, 2-, 3- or 4-methoxybut-1-yl, 2-ethoxyethy-1-yl, 2-ethoxyprop-1-yl, 3-ethoxyprop-1-yl, und 2-, 3- or 4-ethoxybut-1-yl.

$R_5$ may be linear or branched in the form of $C_1$–$C_6$alkanoyloxy-$C_1$–$C_6$alkyl. The alkanoyloxy group preferably comprises 1 to 4 C-atoms and the alkyl group preferably 2 to 4 C-atoms. Some examples are formyloxymethyl, formyloxyethyl, acetyloxyethyl, propionyloxyethyl and butyroyloxyethyl.

$R_5$ may be linear or branched in the form of $C_1$–$C_6$aminoalkyl and preferably comprise 2 to 4 C-atoms. Some examples are 2-aminoethyl, 2- or 3-aminoprop-1-yl and 2-, 3- or 4-aminobut-1-yl.

$R_5$ may be linear or branched in the form of $C_1$–$C_6$alkylamino-$C_1$–$C_6$alkyl and $C_1$–$C_6$dialkylamino-$C_1$–$C_6$-alkyl. The alkylamino group preferably comprises $C_1$–$C_4$alkyl groups and the alkyl group preferably 2 to 4 C-atoms. Some examples are 2-methylaminoeth-1-yl, 2-dimethylaminoeth-1-yl, 2-ethylaminoeth-1-yl, 2-ethylaminoeth-1-yl, 3-methylaminoprop-1-yl, 3-dimethylaminoprop-1-yl, 4-methylaminobut-1-yl and 4-dimethylaminobut-1-yl.

$R_5$ may be linear or branched in the form of $C_1$–$C_6$alkanoylamido-$C_1$–$C_6$alkyl. The alkanoyloxy group preferably comprises 1 to 4 C-atoms and the alkyl group preferably 1 to 4 C-atoms. Some examples are 2-formamidoeth-1-yl, 2-acetamidoeth-1-yl, 3-propionylamidoeth-1-yl and 4-butyroylamidoeth-1-yl.

$R_5$ may be linear or branched in the form of HO(O)C—$C_1$–$C_6$alkyl and the alkyl group preferably comprises 2 to 4 C-atoms. Some examples are carboxymethyl, carboxyethyl, carboxypropyl and carboxybutyl.

$R_5$ may be linear or branched in the form of $C_1$–$C_6$-alkyl-O—(O)C—$C_1$–$C_6$alkyl, and the alkyl groups preferably comprise independently of one another 1 to 4 C-atoms. Some examples are methoxycarbonylmethyl, 2-methoxycarbonyleth-1-yl, 3-methoxycarbonylprop-1-yl, 4-methoxycarbonylbut-1-yl, ethoxycarbonylmethyl, 2-ethoxycarbonyleth-1-yl, 3-ethoxycarbonylprop-1-yl, and 4-ethoxycarbonylbut-1-yl.

$R_5$ may be linear or branched in the form of $H_2N$—C(O)—$C_1$–$C_6$alkyl, and the alkyl group preferably comprises 2 to 6 C-atoms. Some examples are carbamidomethyl, 2-carbamidoeth-1-yl, 2-carbamido-2,2-dimethyleth-1-yl, 2- or 3-carbamidoprop-1-yl, 2-, 3- or 4-carbamidobut-1-yl, 3-carbamido-2-methylprop-1-yl, 3-carbamido-1,2-dimethylprop-1-yl, 3-carbamido-3-methylprop-1-yl, 3-carbamido-2,2-dimethylprop-1-yl, 2-, 3-, 4- or 5-carbamidopent-1-yl, 4-carbamido-3,3- or -2,2-dimethylbut-1-yl.

$R_5$ may be linear or branched in the form of $C_1$–$C_6$alkyl-HN—C(O)—$C_1$–$C_6$-alkyl or ($C_1$–$C_6$alkyl)$_2$N—C(O)—$C_1$–$C_6$-alkyl, and the NH-alkyl group preferably comprises 1 to 4 C-atoms and the alkyl group preferably 2 to 6 C-atoms. Examples are the carbamidoalkyl groups defined hereinabove, whose N-atom is substituted with one or two methyl, ethyl, propyl or butyl.

A preferred subgroup of compounds of formula I is that in which $R_1$ is $C_1$–$C_4$alkoxy or $C_1$–$C_4$alkoxy-$C_1$–$C_4$alkyloxy, $R_2$ is $C_1$–$C_4$alkoxy, $R_3$ is $C_1$–$C_4$alkyl, $R_4$ is $C_1$–$C_4$alkyl and $R_5$ is $H_2NC(O)$—$C_1$–$C_6$alkyl which if necessary is N-monosubstituted or N-di-$C_1$–$C_4$alkyl substituted.

A more preferred subgroup of compounds of formula I is that in which $R_1$ is methoxy-$C_2$–$C_4$-alkyloxy, $R_2$ is methoxy or ethoxy, $R_3$ is $C_2$–$C_4$alkyl, $R_4$ is $C_2$–$C_4$alkyl and $R_5$ is $H_2NC(O)$—$C_1$–$C_6$alkyl.

An especially preferred compound of formula I is that in which $R_1$ is 3-methoxy-prop-3-yloxy, $R_2$ is methoxy, $R_3$ and $R_4$ are 1-methyleth-1-yl, and $R_5$ is $H_2NC(O)$—[C(CH$_3$)$_2$]—CH$_2$—.

The compounds of formula I show 4 stereogenic C-atoms. According to the invention, all possible diastereomers and any mixtures are included. Preference is for 2(S),4(S),5(S), 7(S)-diastereomers of formula Ia

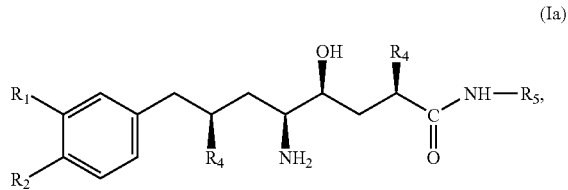

(Ia)

wherein $R_1$, $R_2$, $R_3$, $R_4$ and $R_5$ are as defined above, including the preferences.

Particularly preferred is the compound of formula Ib,

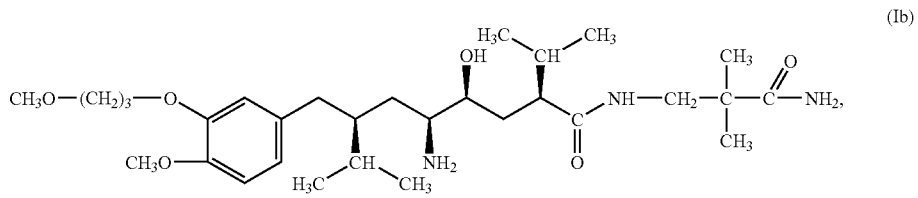

(Ib)

The desired diastereomers may be isolated from the mixtures using chromatographic methods or fractionated crystallization or obtained by means of asymmetric synthesis.

$R_6$ and $R_7$ in formula II may be branched and preferably linear in the form of alkyl and are preferably $C_1$–$C_4$alkyl, for example methyl or ethyl. $R_7$ as alkoxy may preferably be linear and is preferably $C_1$–$C_4$alkoxy, for example methoxy or ethoxy. $R_6$ and $R_7$ together are preferably tetramethylene, —$CH_2CH_2$—O—C(O)— or —CH($CH_2C_6H_5$)$CH_2$—O—C(O)—.

The individual process steps may be carried out in the presence of solvent. Suitable solvents are water and organic solvents, especially polar organic solvents, which can also be used as mixtures of at least two solvents. Examples of solvents are hydrocarbons (petroleum ether, pentane, hexane, cyclohexane, methylcyclohexane, benzene, toluene, xylene), halogenated hydrocarbon (methylene chloride, chloroform, tetrachloroethane, chlorobenzene); ether (diethyl ether, dibutyl ether, tetrahydrofuran, dioxane, ethylene glycol dimethyl or diethyl ether); carboxylic acid ester and lactone (methyl acetate, ethyl acetate, methyl propionate, valerolactone); N,N-substituted carboxamides and lactams (dimethylformamide, dimethylacetamide, N-methylpyrrolidone); ketones (acetone, methylisobutylketone, cyclohexanone); sulfoxides and sulfones (dimethylsulfoxide, dimethylsulfone, tetramethylene sulfone); alcohols (methanol, ethanol, n- or i-propanol, n-, i- or t-butanol, pentanol, hexanol, cyclohexanol, cyclohexanediol, hydroxymethyl or dihydroxymethyl cyclohexane, benzyl alcohol, ethylene glycol, diethylene glycol, propanediol, butanediol, ethylene glycol monomethyl or monoethyl ether, and diethylene glycol monomethyl or monoethyl ether; nitriles (acetonitrile, propionitrile); tertiary amines (trimethyl-, triethyl-, tripropyl- and tributylamine, pyridine, N-methylpyrrolidine, N-methylpiperazine, N-methylmorpholine) and organic acids (acetic acid, formic acid).

Process Step a)

Suitable chlorination, bromination and iodination agents are elemental bromine and iodine, in particular N-chlorine, N-bromine and N-iodocarboxamides and dicarboximides. Preferred are N-chloro, N-bromo and N-iodophthalimide and especially chloro, N-bromo and N-iodosuccinimide, as well as tertiary butyl hypochlorite and N-halogenated sulfonamides and imides, for example chloroamine T. It is of advantage to carry out the reaction in organic solvents. The reaction temperature may range for example from approximately –70° C. to ambient temperature and preferably from –30° C. to 10° C. Carboxamides are advantageously lactonized in the presence of inorganic or organic acids, at least equimolar quantities of water, and reacted in the presence of water-miscible solvents, for example tetrahydrofuran or dioxane. Suitable acids are for example formic acid, acetic acid, methanesulfonic acid, trifluoroacetic acid, trifluoromethanesulfonic acid, toluenesulfonic acid, $H_2SO_4$, $H_3PO_4$, hydrogen halides, acid ion exchange resins, and acids immobilized on solid carriers. Water is generally used in at least equimolar quantities.

In this process step, if compounds of formula IIa

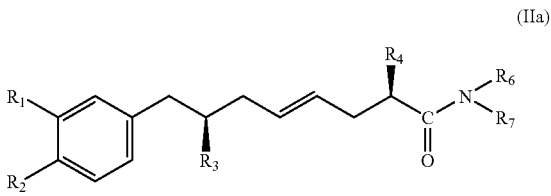

(IIa)

are used, compounds of formula IIIa are obtained

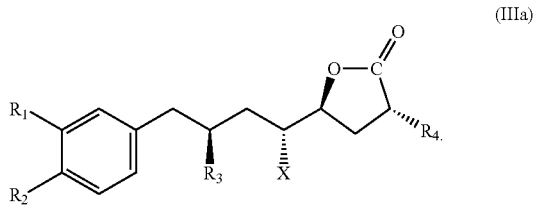

(IIIa)

Process Step b)

Suitable azidation agents are for example metal azides, especially alkaline earth metal azides and alkali metal azides, as well as silyl azides. Especially preferred azidation agents are lithium azide, sodium azide and potassium azide. The reaction may be carried out in organic solvents, advantageously in water-miscible solvents mixed with water, typically for example alcohols or ethers (methanol, ethanol, ethylene glycol, diethylene glycol, diethylene glycol monomethyl or ethyl ether, diethyl ether, tetrahydrofuran, dioxane). The reaction temperature may range for example from approximately 20° C. to 150° C. and preferably from 50° C. to 120° C. It may be expedient to include the use of phase transfer catalysts. The preparation and synthetic use of azides are described for example by E. F. V. Scriven in Chemical Reviews, Vol. 88 (1988), pages 298 to 317.

If compounds of formula IIIa are used, compounds of the formula IVa are obtained

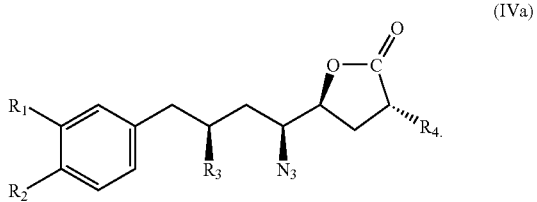
(IVa)

Process Step c)

The reaction of compounds of formula IV or IVa with a compound $R_5NH_2$ by opening of the lactone ring is expediently carried out in the presence of alcohols or amines which are capable of forming activated carboxylic acid esters or carboxamides. Such compounds are well-known. It may be 2-hydroxypyridine, N-hydroxycarboxamides and imides, and carboximide (N-hydroxysuccinimide). Organic solvents are used as solvent, tertiary amines being of advantage, for example trimethyl or triethyl amines. The reaction temperature may range for example from approximately 40° C. to 150° C. and preferably from 50° C. to 120° C.

If compounds of formula IVa are used, compounds of formula Va are obtained in the reaction.

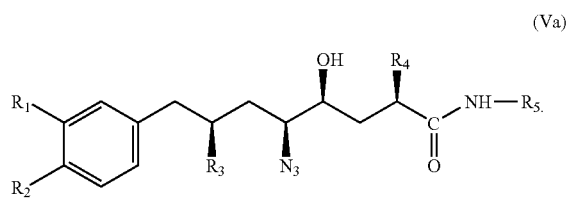
(Va)

Process Step d)

Reduction of the azide group to the amine group in the compounds of formulae V or Va takes place in a manner known per se (see Chemical Reviews, Vol. 88 (1988), pages 298 to 317), for example using metal hydrides or more expediently using a catalytic method with hydrogen in the presence of homogeneous (Wilkinson catalyst) or heterogeneous catalysts, for example Raney nickel or precious metal catalysts such as platinum or palladium, if necessary on substrates such as carbon. The hydrogenation can also be carried out if necessary catalytically under phase transfer conditions, for example with ammonium formate as hydrogen donor. It is of advantage to use organic solvents. The reaction temperature may range for example from approximately 0° C. to 200° C. and preferably from 10° C. to 100° C. Hydrogenation may be carried out at normal pressure or increased pressure up 100 bar, for example, and preferably up to 50 bar.

If compounds of formula Va are used, compounds of formula Ia are obtained.

The compounds of formula I may be converted to addition salts in a manner known per se by treatment with monobasic or polybasic, inorganic or organic acids. Hemifumarates are preferred.

The halolactonization of process step a), the azidation of process step b), and the azide reduction of process step d) are described by P. Herold in the Journal of Organic Chemistry, Vol. 54 (1989), pages 1178–1185.

The intermediate products of formulae II, IIa, III and IIIa are new and represent further objects of the invention.

A further object of the invention is thus represented by compounds of formula II

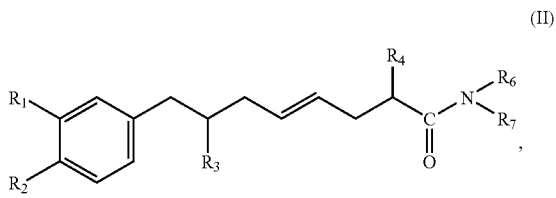
(II)

and in particular of formula IIa

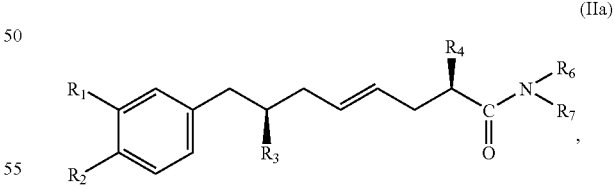
(IIa)

wherein $R_1$, $R_2$, $R_3$, $R_4$, $R_6$ and $R_7$ are as defined above, including the preferences. In an especially preferred embodiment, $R_1$ is 1-methoxyprop-3-yloxy, $R_2$ is methoxy, $R_3$ and $R_4$ are isopropyl and $R_6$ is methyl or ethyl, $R_7$ is methyl, ethyl or methoxy, or $R_6$ and $R_7$ together are tetramethylene, pentamethylene or —CH(CH$_2$C$_6$H$_5$)CH$_2$—O—C(O)—.

A further object of the invention is thus represented by compounds of formula III

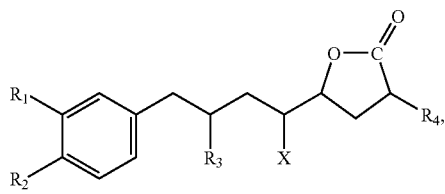

and preferably compounds of formula IIIa

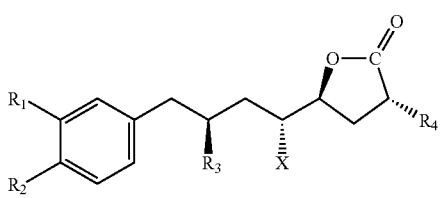

wherein $R_1$, $R_2$, $R_3$, $R_4$ and X are as defined above, including the preferences. In an especially preferred embodiment, $R_1$ is 1-methoxyprop-3-yloxy, $R_2$ is methoxy, $R_3$ and $R_4$ are isopropyl and X is Cl; Br or I.

The compounds of formula II are obtainable by reacting a compound of formula VI

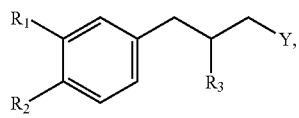

as racemate or enantiomer, with a compound of formula VII, as racemate or enantiomer,

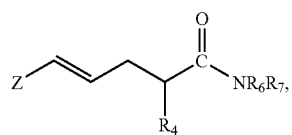

wherein $R_1$ to $R_4$, $R_6$ and $R_7$ are as defined above, including the preferences, Y is Cl, Br or I and Z is Cl, Br or I, in the presence of an alkali metal or alkaline earth metal. Y and Z are preferably Br and especially Cl.

The coupling of Grignard reagents with alkenyl halides in an ether such as, for example, tetrahydrofuran or dioxan as solvents in the presence of catalytic quantities of a soluble metal complex, for example an iron complex such as iron acetonyl acetate, and in the presence of more than equimolar quantities of a solvent stabilizing the metal complex, for example n-methylpyrrolidone, is described by G. Cahiez et al. in Synthesis (1998), pages 1199–1200. The reaction temperature may for example be −50 to 80° C., preferably −20 to 50° C. Catalytic quantities may for example be 0.1 to 20% by weight in relation to a compound of formula VIII. It is expedient to carry out the reaction so that initially a compound of formula VI is converted to a Grignard compound (for example with magnesium) and then adding a solution of a compound of formula VII, metal complex and N-methylpyrrolidone, or vice versa.

It was surprisingly found to be of advantage when only catalytic quantities of a solvent stabilizing the metal complex, for example N-methylpyrrolidone, were used. Catalytic quantities may for example be 1 to 10 mol percent, preferably 1 to 5 mol percent, in relation to the compounds of formulae VI or VII.

Compounds of formula VI in the form of their racemates or enantiomers are known or capable of being prepared according to analogous processes. For example, $R_1R_2$phenylaldehyde may be reacted with $R_3$diethoxyphosphorylacetic acid ester to form 2-$R_3$-3-($R_1R_2$phenyl)acrylic acid esters, these then hydrogenated to form the corresponding propionic acid esters, the ester group saponified and the carboxylic acid reduced to alcohol, and finally the hydroxyl group substituted with halogen. Enantiomers are obtainable by separating the racemates of the carboxylic acids with for example quinine or by enzymatic resolution of the racemates of the corresponding carboxylic acid esters. Details are described in the examples. A possible asymmetric synthesis of compounds of formula VI is described in EP-A-0 678.503.

The compounds of formula VII in form of their racemates or enantiomers are new and are a further obbject of the invention. They may be prepared by the reaction of metalled isovaleric acid esters (for example lithium isovaleric acid esters) with 1,3-transhalogenpropene, followied by halogenation of the resulting carboxylic acid to form the acid halide and reaction with a secondary amine. The coupling of isovaleric acid with 1,3-trans-halogenpropene can be carried out asymmetrically according to a method described by D. A. Evans in Asymmetric Synthesis, Vol. 3, 1984 (Academic Press Inc.), pages 2–110. Details are described in the examples. Enantiomers are obtainable by separating the racemates of the carboxylic acids with for example cinchonidine or by enzymatic resolution of the racemates of the corresponding carboxylic acid esters. Details are described in the examples.

A further object of the invention is represented by compounds of formula VII in the form of their racemates or enantiomers

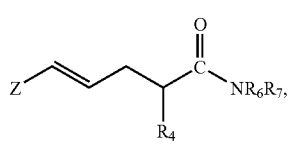

and preferably compounds of formula VIIa

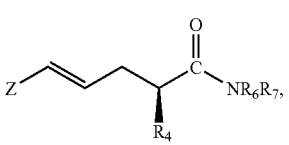

wherein $R_4$, $R_6$ and $R_7$ are as defined above, including the preferences, and Z is Cl, Br or I and preferably Cl.

With the choice of intermediate products of formula II, the compounds of formula I, which per se are complex compounds, can be prepared in a convergent and simple manner, which is especially true also of enantioselective or diastereoselective synthesis. The total yield from process steps a) to d) may amount to 25% and even 30% or more, which makes industrial application feasible.

The following examples explain the invention in more detail.

A) Preparation of Compounds of Formula VI

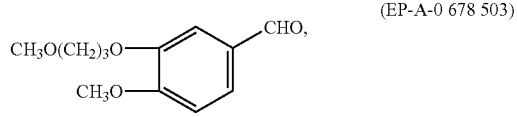
(EP-A-0 678 503)

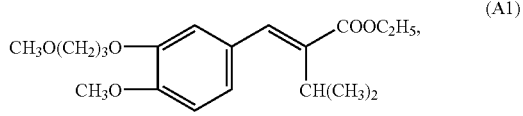
(A1)

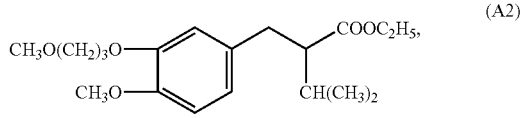
(A2)

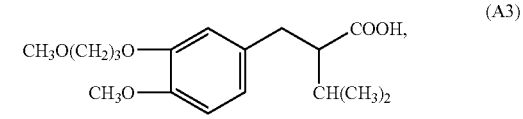
(A3)

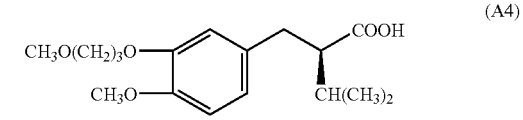
(A4)

EXAMPLE A1

A solution of 44.5 g 2-(diethoxyphosphoryl)-3-methylbutyric acid ethyl ester in 60 ml tetrahydrofuran is added dropwise at ambient temperature over a period of 20 minutes to a mixture of 18.8 g potassium tert-butylate and 360 ml tetrahydrofuran. After a further 30 minutes, a solution of 25.0 g 4-methoxy-3-(3-methoxypropoxy)benzaldehyde (EP 0 678 503) in 100 ml tetrahydrofuran is added dropwise. After 14 hours, the reaction mixture is evaporated on a rotary evaporator (Rotavapor) and the residue extracted between diethyl ether (3×), water (1×) and saturated aqueous sodium chloride solution. The combined organic phases are dried, filtered with sodium sulfate and concentrated by evaporation on the Rotavapor. By means of flash chromatography ($SiO_2$ 60F/ethyl acetate/hexane 2:3), title compound A1 is obtained from the residue as a slightly yellowish oil (28.4 g, 75%): $^1$H-NMR (400 MHz, $CDCl_3$, δ): 1.15–1.42 (m, 9H), 2.12 (m, 2H), 2.70–3.30 (m, 1H), 3.40 (s, 3H), 3.60 (m, 2H), 3.85–4.35 (m, 7H), 6.40–7.50 (m, 4H) ppm.

EXAMPLE A2

26 g A1 is hydrogenated in the presence of 13 g RaNi in 500 ml ethanol for 6 hours at ambient temperature and normal pressure. The reaction mixture is filtered and evaporated on a Rotavapor. By means of flash chromatography ($SiO_2$ 60F/ethyl acetate/hexane 1:1), title compound A2 is obtained from the residue as a colourless oil (24.7 g, 94%): $^1$H-NMR (400 Hz, $CDCl_3$, δ): 1.00 (d, 3H), 1.04 (d, 3H), 1.13 (t, 3H), 1.92 (m, 1H), 2.12 (m, 2H), 2.47 (m, 1H), 2.80 (m, 2H), 3.38 (s, 3H), 3.60 (t, 2H), 3.82 (s, 3H), 4.05 (m, 2H), 4.12 (t, 2H), 6.68–6.80 (m, 3H) ppm.

EXAMPLE A3

A mixture of 27 g A2, 60 ml ethanol and 60 ml 2N sodium hydroxide solution is agitated for 24 hours under reflux. The reaction mixture is taken up in 100 ml water and washed with diethyl ether (2×200 ml). The aqueous phase is acidified with 2N hydrochloric acid and extracted with ethyl acetate (4×). The combined organic phases are dried, filtered with sodium sulfate and concentrated by evaporation on the Rotavapor. By means of flash chromatography ($SiO_2$ 60F/ dichloromethane/methanol 20:1), title compound A3 is obtained from the residue as a slightly yellowish oil (23.1 g, 93%): $^1$H-NMR (400 MHz, $CDCl_3$, δ): 0.90–1.00 (m, 6H), 1.80 (m, 1H), 1.95 (m, 1H), 1.95 (m, 1H), 2.35 (m, 1H), 2.70 (m, 2H), 3.30 (s, 3H), 3.50 (t, 2H), 3.75 (s, 3H), 3.98 (t, 2H), 6.60–6.90 (m, 3H), 11.95 (s, 1H) ppm.

EXAMPLE A4

Racemate Resolution of Compound A3

5.0 g A3 is dissolved in 15 ml isopropanol and 210 ml diisopropyl ether. After addition of 2.61 g quinine and 1.235 ml triethylamine, the mixture is heated in an oil bath to 50° C. under agitation. The oil bath is then removed, and the clear solution with 220 mg finely pulverized salt of A4 is inoculated with quinine. Agitation is continued for 2 hours at ambient temperature and then for another 2 hours under ice cooling. The precipitate is filtered off, washed with twice 50 ml ice-cold diisopropyl ether and then dried in a vacuum at 50° C. until constant weight is attained. 4.22 g enriched salt of A4 with quinine is obtained; melting point 123° C. The salt obtained in this way is distributed between 250 ml diethyl ether and 50 ml 1 N HCl. The aqueous phase is separated, the organic phase washed with saturated NaCl solution, dried with MgSO₄ and concentrated by evaporation in a vacuum. 2.22 g (44.4%) of the enriched compound A4 is obtained.

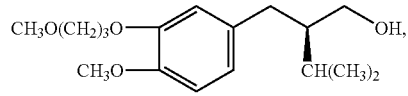
(EP-A-0 678 503)

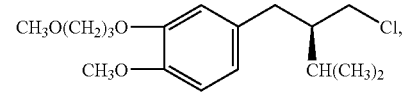
(A5)

EXAMPLE 5

An agitated solution of 174 g 2R-[4-methoxy-3-(3-methoxypropoxy)benzyl]-3-methylbutan-1-ol [EP 0678 503] and 1.31 carbon tetrachloride is cooled to 10° C. 393 ml trioctylphosphine is added dropwise, and the reaction solution is then agitated for 16 hours at ambient temperature. The mixture is completely concentrated by evaporation and the residue extracted between dichloromethane (3×) and water (1×). The combined organic phases are dried with magnesium sulfate, filtered and concentrated by evaporation. The residue is purified by means of flash chromatography (SiO₂ 60F/ethyl acetate/hexane 1:9), and title compound A5 is obtained after crystallization (hexane at −50° C.) as a white solid (152.3 g, 82%): melting point 51–52° C.; ¹H-NMR (400 MHz, CDCl₃, δ): 1.0 (m, 6H), 1.71 (m, 1H), 1.93 (m, 1H), 2.12 (m, 2H), 2.35 (m, 1H), 2.77 (m, 1H), 3.39 (s, 3H), 3.40–3.55 (m, 2H), 3.71 (t, 2H), 3.87 (s; 3H), 4.13 (m, 3H), 6.65–6.85 (m, 3H) ppm.

B) Preparation of Compounds of Formula VII

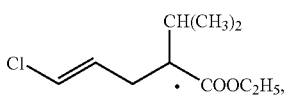
(B1)

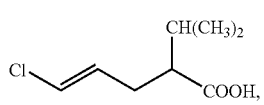
(B2)

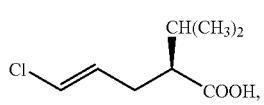
(B3)

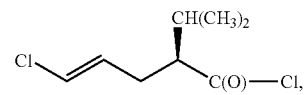
(B5)

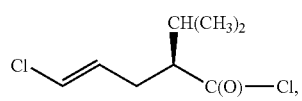

B6: R = N(CH3)2
B7: R = N(C5H5)2
B8: R = N(OCH3)(CH3),

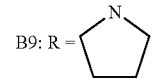
B9: R =

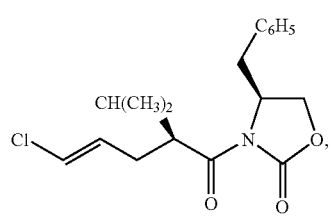
(B4)

EXAMPLE B1

An agitated solution of 24.9 ml diisopropylamine and 240 ml tetrahydrofuran is cooled to minus 15° C., and 100 ml 1.6 M n-butyl lithium solution (in hexane) is added over a period of 10 minutes. The solution is stirred for 30 minutes at −15° C. and then, over a period 30 minutes, a solution of 24.1 ml ethyl isovalerate in 80 ml tetrahydrofuran is added dropwise. The mixture is agitated for a further 5 minutes at −15° C., and then 19.5 g trans-1,3-dichloropropene and 2.4 g sodium iodide are added consecutively. The reaction mixture is agitated for a further 16 hours at ambient temperature, and then 500 ml 10% aqueous ammonium chloride solution is added. The mixture is extracted with diethyl ether (3×) and the organic phases washed consecutively with water (1×), 0.1 M sodium thiosulfate solution (1×) and brine (1×). The combined organic phases are dried with sodium sulfate and concentrated by evaporation. By means of distillation, title compound B1 is obtained as a colourless oil (24.8 g, 76%). ¹H-NMR (400 MHz, CDCl₃, δ): 0.95 (m, 6H), 1.30 (t, 3H), 1.92 (m, 1H), 2.20–2.40 (m, 3H), 4.20 (m, 2H), 5.80–6.10 (m, 2H) ppm.

EXAMPLE B2

A solution of 150.2 g B1, 500 ml ethanol and 500 ml 2N sodium hydroxide solution is agitated for 18 hours under reflux. The ethanol is evaporated from the reaction mixture, the aqueous solution acidified with 1N hydrochloric acid and extracted with diethyl ether (3×). The organic phases are dried with magnesium sulfate and concentrated by evaporation. By means of flash chromatography (SiO₂ 60F/dichloromethane/methanol 20:1), title compound B2 is obtained from the residue as a slightly orange oil (83.7 g, 65%): $^1$H-NMR (400 MHz, CDCl$_3$, δ): 1.03 (m, 6H), 1.98 (m, 1H), 2.20–2.45 (m, 3H), 5.80–6.10 (m, 2H) ppm.

EXAMPLE 3a

Racemate Resolution of Compound B2

5.0 g B2, 5.0 g cinchonidine and 1.98 ml triethylamine are transferred to 150 ml tetrahydrofuran and agitated for 15 minutes under reflux. The oil bath is removed and the clear solution with a salt of B3 is inoculated with cinchonidine. Agitation is continued for 1 hour at ambient temperature and then for another 1 hour under ice cooling. The precipitate is filtered off, washed with twice 25 ml ice-cold acetone and then dried in a vacuum at 50° C. until constant weight is attained. 6.16 g (46.3%) of the enriched salt of B3 is obtained with cinchonidine; melting point 149° C. After double recrystallization from acetone, 4.20 g (31.6%) of the enriched salt of B3 is obtained with cinchonidine, melting point 155° C. The salt obtained in this way is distributed between 250 ml diethyl ether and 50 ml 1 N HCl. The aqueous phase is separated, the organic phase washed with saturated NaCl solution, dried with MgSO$_4$ and concentrated by evaporation in a vacuum. 1.58 g (31.6%) of enriched compound B3 is obtained as colourless oil.

EXAMPLE B3b

Asymmetric Synthesis of B3

To a solution of 155 g B4, 1.3 l tetrahydrofuran and 0.44 l water, agitated at 0° C., 315 ml 30% hydrogen peroxide solution is added dropwise over a period of 15 minutes. 22.1 g lithium hydroxide is added to the reaction mixture, then the cooling bath is removed and agitation is continued for 5 hours at 0–20° C. The reaction mixture is cooled again to 0° C., and a solution of 350 g sodium sulfite in 1.4 l water is added dropwise over a period of 30 minutes. The pH is adjusted to 9.8 by the addition of sodium hydrogencarbonate. The reaction mixture is filtered until clear and tetrahydrofuran evaporated from the filtrate. The aqueous solution obtained is washed with dichloromethane (3×3 l). The pH of the aqueous phase is adjusted to 3.0 with aqueous hydrochloric acid and then extracted with dichloromethane (3×2l). The organic phases are dried with magnesium sulfate and concentrated by evaporation on the Rotavapor. By means of distillation, title compound B3 is obtained from the residue as a colourless oil. (142 g, 87%). $^1$H-NMR (400 MHz, CDCl$_3$, δ): 1.02 (m, 6H), 1.98 (m, 1H), 2.25–2.45 (m, 3H), 5.85–6.10 (m, 2H) ppm.

EXAMPLE B4

A solution of 290 g 4S-benzyl-3-(3-methylbutyryl)oxazolidin-2-one in 0.58 l tetrahydrofuran is cooled to −78° C., and 1.14 l 1 M lithium hexamethyldisilazide (in tetrahydrofuran) is added dropwise over a period of 65 minutes. The mixture is agitated for another hour at −78° C., and a prepared solution of trans-1-chloro-3-iodopropene in tetrahydrofuran is then added. The temperature is allowed to increase to 0° C. and agitation is continued for a further 20 hours. 500 ml 10% ammonium chloride solution is added to the reaction mixture, which is then extracted with diethyl ether (2×1 l). The organic phases are washed with water (1×1 l), dried with sodium sulfate and concentrated by evaporation. By means of flash chromatography (SiO$_2$ 60F/ ethyl acetate/hexane 5:1), title compound B4 is obtained from the residue as a slightly orange oil (582 g, 78%): $^1$H-NMR (400 MHz, CDCl$_3$, δ): 0.85 (m, 6H), 2.02(m, 1H), 2.3–2.55 (m, 2H), 2.75 (m, 1H), 3.30 (m, 1H), 3.88 (m, 1H), 4.18 (m, 2H), 4.70 (m, 1H), 5.80–6.10 (m, 2H), 7.15–7.40 (m, 5H) ppm.

Preparation of trans-1-chloro-3-propene. 266.1 g sodium iodide is added to a solution of 184.7 g trans-1,3-dichloropropene in 0.58 l tetrahydrofuran and the mixture agitated for 30 minutes under exclusion of light at ambient temperature. The mixture is filtered until clear and the filtrate used in the crude state.

EXAMPLE B5

4.42 ml oxalyl chloride is added to a solution of 4.54 g B3 in 25 ml toluene at ambient temperature. The reaction mixture is agitated for 15 minutes at ambient temperature, and then 0.052 ml N,N-dimethylformamide over a period of 1 minute. The reaction mixture is heated to reflux and agitated for 1 hour. The reaction solution is concentrated by evaporation and the residue distilled. Title compound B5 is obtained as a colourless oil. (4.43 g, 88%). $^1$H-NMR (400 MHz, CDCl$_3$, δ): 1.02 (d, 3H), 1.08 (d, 3H), 2.16 (m, 1H), 2.40 (m, 1H), 2.45 (m, 1H), 2.68 (m, 1H), 5.80–6.10 (m, 2H) ppm.

EXAMPLE B6

A solution of 1.53 g dimethylamine, 3.66 ml pyridine and 25 ml dichloromethane is cooled to 0° C., and then 4.42 g B5 in 25 ml dichloromethane is added dropwise at 0 to −10° C. The reaction mixture is agitated for a further 2 hours at 0° C. and then concentrated by evaporation on the Rotavapor. The residue is distributed between diethyl ether (2×) and 2N hydrochloric acid (3×), saturated sodium hydrogencarbonate solution (1×) and saturated saline solution. The organic fractions are combined, dried over sodium sulfate and concentrated. The residue is distilled, and title compound B6 is obtained as a colourless oil. (4.13 g, 89%). [α]$^{25}_D$ -7.3 (c 1, chloroform). $^1$H-NMR (400 MHz, CDCl$_3$, δ): 0.90 (d, 3H), 0.95 (d, 3H), 1.92 (m, 1H), 2.20–2.30 (m, 1H), 2.35–2.50 (m, 2H), 2.98 (s, 3H), 3.04 (s, 3H), 5.80–6.10 (m, 2H) ppm.

Derivatives B7, B8 and B9 are prepared from the acid chloride B5 and the corresponding amines in the manner described in example B6.

C) Preparation of Compounds of Formula II

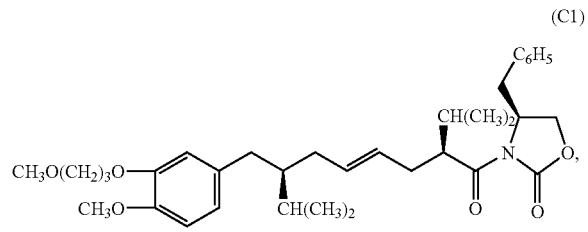

(C1)

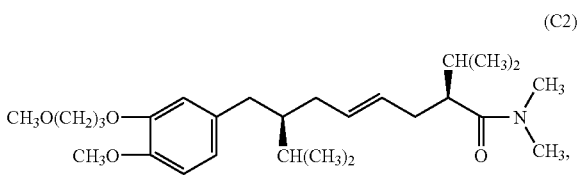

(C2)

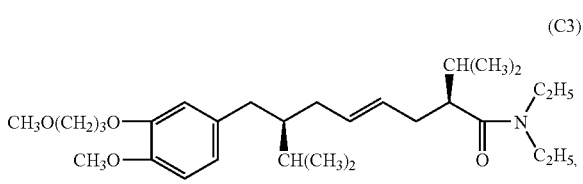

(C3)

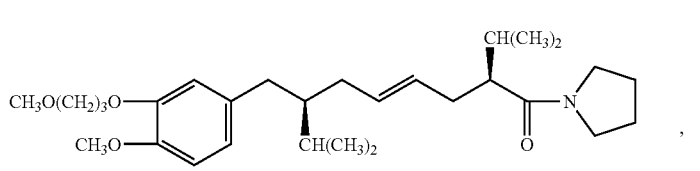

(C4)

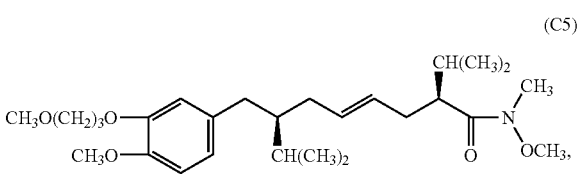

(C5)

EXAMPLE C1

A mixture of 4.28 g magnesium powder and 50 ml tetrahydrofuran is heated to 60° C., and 0.30 ml 1,2-dibromoethane then added over a period of 2 minutes (visible exothermic reaction). A solution of 13.85 g A5, 1.6 ml 1,2-dibromoethane and 130 ml tetrahydrofuran is added dropwise over a period of 15 minutes at 60–64° C. The mixture is agitated for another 30 minutes under reflux and then cooled down to ambient temperature. The reaction mixture is filtered under argon until clear and the filtrate cooled in a second reaction vessel to −2° C. A solution of 13.43 g B4, 0.71 g iron(III) acetylacetonate, 0.192 ml N-methylpyrrolidone and 80 ml tetrahydrofuran is added dropwise over a period of 2 minutes at −2 to 5° C. The reaction mixture is agitated for a further 10 minutes at 0° C., and 140 ml 2H hydrochloric acid is then added. The mixture is extracted with diethyl ether (2×) and the organic phases washed consecutively with water (1×) and saturated aqueous sodium chloride solution (1×). The combined organic phases are dried, filtered with sodium sulfate and concentrated by evaporation on the Rotavapor. By means of flash chromatography (SiO$_2$ 60F/diethyl ether/hexane 1:1), title compound C1 is obtained from the residue as a colourless oil (13.7 g, 59%): TLC R$_f$=0.11 (diethyl ether/hexane 1:1); $^1$H-NMR (500 MHz, CDCl$_3$, δ): 0.81–0.90 (m, 6H), 0.97 (d, 6H), 1.52 (m, 1H), 1.70 (m, 1H), 1.84–1.91 (m, 1H), 1.93–2.03 (m, 2H), 2.08 (m, 2H), 2.31–2.39 (m, 2), 2.41–2.59 (m, 3H), 3.29 (dd, 1H), 3.36 (s, 3H), 3.57 (t, 2H), 3.80 (s, 3H), 3.78–3.85 (m, 1H), 4.03–4.16 (m, 4H), 4.67 (m, 1H), 5.37–5.5. (m, 2H), 6.63 (dd, 1H), 6.67 (d, 1H), 6.70 (d, 1H), 7.14–7.34 (m, 5H) ppm.

EXAMPLE C2

A mixture of 10.7 g magnesium powder and 120 ml tetrahydrofuran is heated to 60° C., and 0.74 ml 1,2-dibromoethane then added over a period of 2 minutes (visible exothermic reaction). A solution of 34.6 g A5, 4.0 ml 1,2-dibromoethane and 320 ml tetrahydrofuran is added dropwise over a period of 15 minutes at 62–64° C. The mixture is agitated for another 30 minutes under reflux and then cooled down to ambient temperature. The reaction mixture is filtered under argon until clear and resulting Grignard solution added dropwise over a period of 10 minutes to a solution of 20.4 g B4, 0.240 ml N-methylpyrrolidone, 0.88 g iron(III) acetylacetonate in 200 ml tetrahydrofuran at −5 to 0° C. The reaction mixture is agitated for a further 15 minutes at 0 to 10° C., and 320 ml 2H hydrochloric acid is then added. The mixture is now extracted with diethyl ether (3×500 ml) and the organic phases washed consecutively with water (1× 400 ml) and saturated aqueous sodium chloride solution (1× 400 ml). The combined organic phases are dried with sodium sulfate, filtered and concentrated by evaporation on the Rotavapor. By means of flash chromatography (SiO$_2$ 60F/ethyl acetate/hexane 2:1), title compound C2 is obtained from the residue as a slightly yellowish oil (36.2 g, 81%): TLC R$_f$=0,09 (diethyl ether/hexane 2:1); $^1$H-NMR (500 MHz, CDCl$_3$, δ): 0.82–0.99 (m, 12H), 1.49 (m, 1H), 1.69 (m, 1H), 1.78–1.98 (m, 3H), 2.10 (m, 2H), 2.17–2.41 (m, 5H), 2.92 (s, 3H), 3.0 (s, 3H), 3.37 (s, 3H), 3.58 (t, 2H), 3.84 (s, 3H), 4.10 (t, 2H), 5.26–5.34 (m, 1H), 5.36–5.44 (m, 1H), 6.64 (m, 2H), 6.78 (d, 1H) ppm.

By analogy with example C2, compounds C3, C4 and C5 are prepared by reacting compound A5 with compounds B7, B8 and B9.

D) Halolactonization

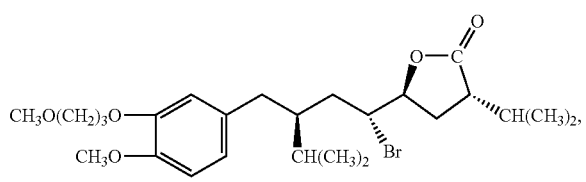

(D1)

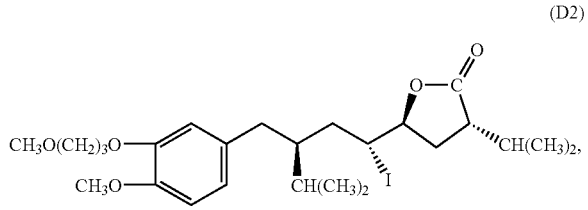

(D2)

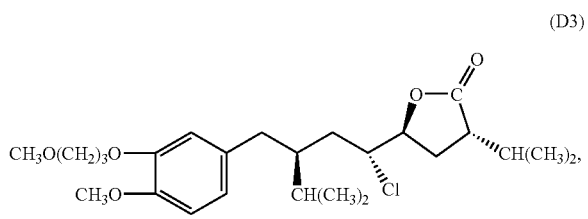

(D3)

EXAMPLE D1

3.85 ml water is added to a solution of 34.2 g C2 and 385 ml tetrahydrofuran, and the mixture cooled to 0° C. while being agitated. Then 10 times 1.03 ml 42.5% o-phosphoric acid and 10 times 1.5 g N-bromosuccinimide are added alternately every 3 minutes. The reaction mixture is agitated for another 90 minutes at 0° C. and then, over a period of 10 minutes, is introduced to 600 ml sodium hydrogen sulfite solution cooled to 0° C. The mixture is agitated for another 15 minutes at 0° C. and then extracted with diethyl ether (1×1 l and 2×0.5 l) The organic phases are washed consecutively with 1N hydrochloric acid (1×0.6 l), water (1×0.6 l), saturated aqueous sodium hydrogencarbonate solution (lx 0.6 l) and brine (lx 0.6 l), dried with sodium sulfate and concentrated by evaporation on the Rotavapor. By crystallization (diisopropyl ether-hexane 1:2 at −25° C.), title compound D1 is obtained as white crystallizate (27.5 g, 72%): Melting point 48–49° C.; TLC $R_f$=0.09 (diethyl ether/hexane 2:1); $[\alpha]^{25}_D$=−44.2 (c 1, chloroform); $^1$H-NMR (500 MHz, CDCl$_3$, δ): 0.85–1.07 (m, 12H), 1.57–1.65 (m, 1H), 1.79–2.00 (m, 3H), 2.07–2.27 (m, 6H), 2.62 (m, 1H), 2.75 (dd, 1H), 3.37 (s, 3H), 3.59 (t, 2H), 3.86 (s, 3H), 4.02 (m, 1H), 4.12 (t, 2H), 4.35 (m, 1H), 6.72 (dd, 1H), 6.75 (d, 1H), 6.81 (d, 1H) ppm. D1 can also be prepared by analogy from C3, C4 and C5.

EXAMPLE D2

0.56 g N-Bromosuccinimide is added to a mixture of 1.72 g C1, 36 ml dichloromethane and 12 ml water and the mixture agitated for 24 hours at 35° C. The organic phase is separated, washed with 0.1 N sodium thiosulfate solution and brine, dried with sodium sulfate and concentrated by evaporation on the Rotavapor. After flash chromatography (SiO$_2$ 60F/diethyl ether/hexane 1:1) and crystallization (diisopropyl ether/hexane 1:2 at −25° C.), title compound D1 is obtained from the residue as white crystallizate (0.61 g, 41%).

Derivatives D2 and D3 are obtained in a similar manner from C2:

D2: $^1$H-NMR (500 MHz, CDCl$_3$, δ): 0.85–1.07 (m, 12H), 1.57–1.66 (m, 1H), 1.69–1.93 (m, 3H), 2.04–2.26 (m, 6H), 2.62 (m, 1H), 2.77 (dd, 1H), 3.37 (s, 3H), 3.59 (t, 2H), 3.86 (s, 3H), 4.20 (m, $_1$H), 4.12 (t, 2H), 4.20 (m, 1H), 6.70 (dd, 1H), 6.73 (d, 1H), 6.80 (d, 1H) ppm.

D3: $^1$H-NMR (500 MHz, CDCl$_3$, δ): 0.85–1.07 (m, 12H), 1.47–1.55 (m, 1H), 1.75–1.97 (m, 3H), 2.07–2.27 (m, 6H), 2.62 (m, 1H), 2.74 (dd, 1H), 3.37 (s, 3H), 3.59 (t, 2H), 3.86 (s, 3H), 3.98 (m, 1H), 4.12 (t, 2H), 4.35 (m, 1H), 6.72 (dd, 1H), 6.75 (d, 1H), 6.81 (d, 1H) ppm.

E) Azidation

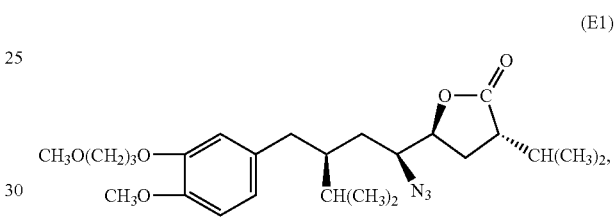

(E1)

EXAMPLE E1

A mixture of 63.1 g D1, 39.0 g sodium azide and 450 ml tripropylene glycol and 150 ml water is agitated for 41 hours at 80° C. The reaction mixture is cooled to ambient temperature, and 30 ml dimethylamino-1-propylamine is added and the mixture then agitated for another 3 hours at ambient temperature. The reaction mixture is poured onto 750 ml water and extracted with tert-butyl methyl ether (3×750 ml). The organic phases are washed consecutively with 750 ml 0.5 N HCl, 750 ml NaHO$_3$ (5% in water), water (3×750 ml) and 750 ml brine. The organic phases are dried with 150 g sodium sulfate, filtered and concentrated by evaporation on the Rotavapor. By means of flash chromatography (SiO$_2$ 60F/ethyl acetate/hexane 1:3), title compound A1 is obtained from the residue as a slightly colourless oil (32.1 g, 58%): 0.89–0.98 (m, 9H), 1.03 (d, 3H), 1.33–1.41 (m, 1H), 1.65–1.85 (m, 3H), 1.91–2.01 (m, 1H), 2.02–2.20 (m, 4H), 2.42–2.49 (m, 1H), 2.55–2.65 (m, 2H), 2.92–2.97 (m, 1H), 3.37 (s, 3H), 3.59 (t, 2H), 3.85 (s, 3H), 4.12 (t, 2H), 4.27 (m, 1H), 6.72 (dd, 1H), 6.75 (d, 1H), 6.81 (d, 1H) ppm.

F) Amidation of Lactone

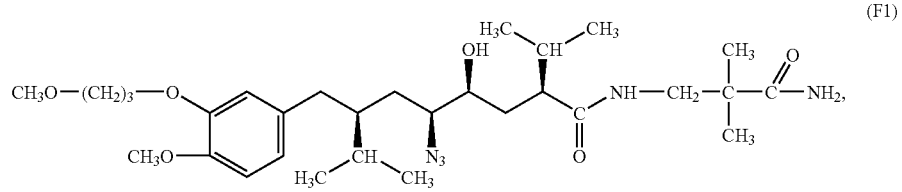

(F1)

EXAMPLE F1

A mixture of 59.1 g (HPLC assay: 93.8%) E1, 41.82 g 3-amino-2,2-dimethylpropionamide, 2.28 g 2-hydroxypyridine in 59.1 ml triethylamine over a period of 16 hours at 90° C. Then 33 ml triethylamine is distilled off over a period of 0.5 hours, and the residue is agitated for a further 8.5 hours at 90° C. The cooled reaction mixture is extracted between ethyl acetate (3×500 ml), saturated aqueous sodium hydrogencarbonate solution (1×500 ml) and saturated sodium chloride solution (1×500 ml). The combined organic phases are dried with 100 g sodium sulfate, filtered and concentrated on the rotary evaporator. The residue is dried and crude title compound F1 is obtained as an oil (78.4 g, quantitative) (HPLC assay: 88.5%): TLC $R_f$=0.13 (ethyl acetate/hexane 4:1); chromatographed sample: TLC $R_f$=0.13 (ethyl acetate/hexane 4:1); $^1$H-NMR (500 MHz, CDCl$_3$, δ): 0.85–0.96 (m, 12H), 1.23 (s, 6H), 1.30–1.40 (m, 1H), 1.53–1.80 (m, 5H), 1.82–1.93 (m, 1H), 2.06–2.14 (m, 3H), 2.45–2.57 (m, 2H), 2.87–2.92 (m, 1H), 3.13 (d, 1H), 3.32–3.52 (m, 3H), 3.36 (s, 3H), 3.59 (t, 2H), 3.84 (s, 3H), 4.12 (t, 2H), 5.51 (bs, 1H), 6.01 (bs, 1H), 6.43 (t, 1H), 6.72 (dd, 1H), 6.75 (d, 1H), 6.81 (d, 1H) ppm.

G) Hydrogenation of the Azide Group

EXAMPLE G1

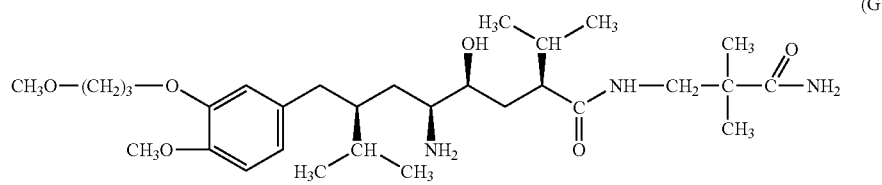

(G1)

78.4 g (HPLC assay: 88.5%) F1 (crude) is hydrogenated for 3 hours in the presence of 3.92 g Pd/C$_5$% and 7.2 ml ethanol amine in 700 ml tert-butyl methyl ether at ambient temperature and 3.0 bar. The reaction mixture is filtered and the catalyst washed with 300 ml tert-butyl methyl ether. The filtrate is washed consecutively with 400 ml 2N NaOH and 400 ml brine. The aqueous phases are then extracted with tert-butyl methyl ether (2×400 ml). The combined organic phases are dried with 100 g sodium sulfate and concentrated by evaporation. The residue is mixed with 7.31 g fumaric acid and dissolved in 200 ml ethanol and filtered until clear. The filtrate is concentrated by evaporation to a total weight of 104 g and dissolved in 1.7 l acetonitrile at 35° C. The resulting solution is inoculated with 10 mg of title compound (hemifumarate) and agitated for 17 hours at ambient temperature. The suspension is cooled to 0° C. and filtered off by suction after 2 hours. The residue is washed with acetonitrile (3×200 ml) and then dried in a vacuum at 35° C. The title compound (hemifumarate) is obtained as white crystals (59.5 g, 81% in relation to E1): $^1$H NMR (360 MHz, DMSO-d$_6$); δ0.7–0.9 (m, 12H), 1.04 (s, 6H), 1.27 (m, 3H), 1.4–1.8 (m, 4H), 1.94 (m, 2H), 2.23 (m, 1H), 2.35 (dd, J=8.4, 8.0 Hz, 1H), 2.45 (m, 1H), 3.08 (m, 2H), 3.2–3.5 (m, 2H), 3.24 (s, 3H), 3.47 (t, J=6.4 Hz, 2H), 3.74 (s, 3H), 3.97 (t, J=6.4 Hz, 2H), 6.37 (s, 1H), 6.68 (dd, J=8.0, 2.0 Hz, 1H), 6.77 (d, J=6 Hz, 1H), 6.80 (bs, 1H), 6.83 (d, J=8 Hz, 1H), 7.13 (bs, 1H), 7.49 (t, J=6 Hz, 1H).

What is claimed is:

1. A compound of formula II

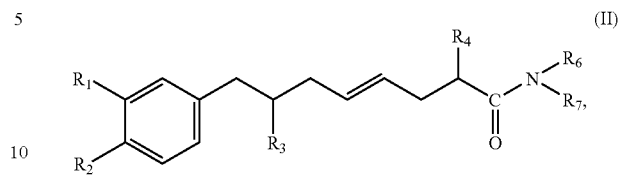

(II)

wherein $R_1$ and $R_2$ are independently of one another H, $C_1$–$C_6$alkyl, $C_1$–$C_6$halogenalkyl, $C_1$–$C_6$alkyloxy, $C_1$–$C_6$alkoxy-$C_1$–$C_6$alkyl or $C_1$–$C_6$alkoxy-$C_1$–$C_6$alkyloxy, $R_3$ is $C_1$–$C_6$alkyl, $R_4$ is $C_1$–$C_6$alkyl, $R_6$ is $C_1$–$C_6$alkyl, and $R_7$ is $C_1$–$C_6$alkyl or $C_1$–$C_6$alkoxy, or $R_6$ and $R_7$ together are tetramethylene, pentamethylene, 3-oxa-1,5-pentylene or —CH$_2$CH$_2$O—C(O)— optionally substituted with $C_1$–$C_4$alkyl, phenyl or benzyl.

2. A compound according to claim 1, wherein $R_1$ is 1-methoxyprop-3-yloxy, $R_2$ is methoxy, $R_3$ and $R_4$ are isopropyl and $R_6$ is methyl or ethyl, $R_7$ is methyl, ethyl or methoxy, or $R_6$ and $R_7$ together are tetramethylene, pentamethylene or —CH(CH$_2$C$_6$H$_5$)CH$_2$—O—C(O)—.

3. A compound according to claim 1, that corresponds to formula IIa

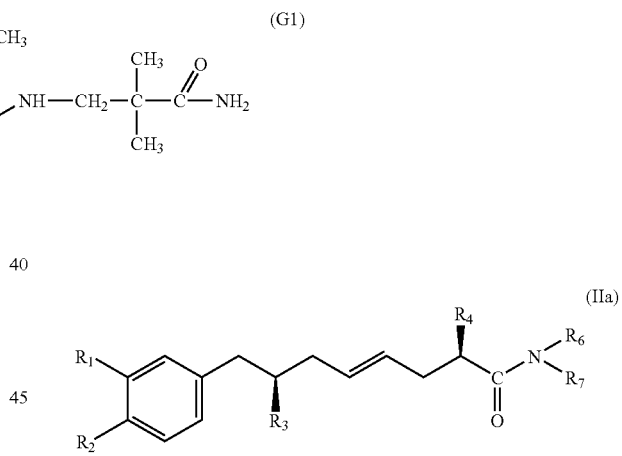

(IIa)

wherein $R_1$ and $R_2$ are independently of one another H, $C_1$–$C_6$alkyl, $C_1$–$C_6$halogenalkyl, $C_1$–$C_6$alkoxy, $C_1$–$C_6$alkoxy-$C_1$–$C_6$alkyl, or $C_1$–$C_6$alkoxy-$C_1$–$C_6$alkyloxy, $R_3$ is $C_1$–$C_6$alkyl, $R_4$ is $C_1$–$C_6$alkyl, $R_6$ is $C_1$–$C_6$alkyl and $R_7$ is $C_1$–$C_6$alkyl or $C_1$–$C_6$alkoxy, or $R_6$ and $R_7$ together are tetramethylene, pentamethylene, 3-oxa-1,5-pentylene or —CH$_2$CH$_2$O—C(O)— optionally substituted with $C_1$–$C_4$alkyl, phenyl or benzyl.

4. A compound of formula III

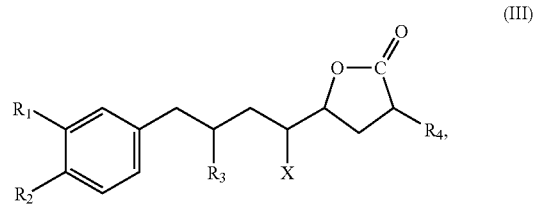

(III)

wherein R₁ and R₂ are independently of one another H, C₁–C₆alkyl, C₁–C₆halogenalkyl, C₁–C₆alkoxy, C₁–C₆alkoxy-C₁–C₆alkyl, or C₁–C₆alkoxy-C₁–C₆alkyloxy, R₃ is C₁–C₆alkyl R₄ is C₁–C₆alkyl, and X is Cl, Br, I or N₃.

5. A compound according to claim 4 wherein R₁ is 1-methoxyprop-3-yloxy, R₂ is methoxy, R₃ and R₄ are isopropyl and X is Cl, Br, I or N₃.

6. A compound according to claim 5, that corresponds to formula IIIa

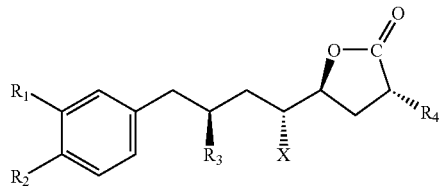

(IIIa)

wherein R₁ and R₂ are independently of one another H, C₁–C₆alkyl, C₁–C₆halogenalkyl, C₁–C₆alkoxy, C₁–C₆alkoxy-C₁–C₆alkyl, or C₁–C₆alkoxy-C₁–C₆alkyloxy, R₃ is C₁–C₆alkyl, R₄ is C₁–C₆alkyl, and X is Cl, Br, I or N₃.

7. A compound of formula VII in the form of its racemate or enantiomer

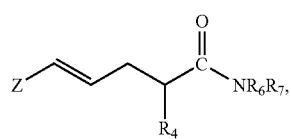

(VII)

wherein R₄ is C₁–C₆alkyl, R₆ is C₁–C₆alkyl, and R₇ is C₁–C₆alkyl or C₁–C₆alkoxy, or R₆ and R₇ together are tetramethylene, pentamethylene, 3-oxa-1,5-pentylene or —CH₂CH₂O—C(O)— optionally substituted with C₁–C₄alkyl, phenyl or benzyl, and Z is Cl, Br or I.

8. A compound according to claim 7, wherein R₄ is 1-methyl ethyl, Z is Cl, and R₆ is methyl or ethyl, R₇ is methyl, ethyl or methoxy, or R₆ and R₇ together are tetramethylene, pentamethylene or —CH(CH₂C₆H₅)CH₂—O—CO—.

9. A compound according to claim 7, that corresponds to formula VIIa

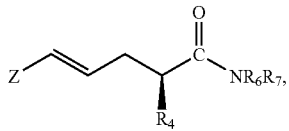

(VIIa)

wherein R₄ is C₁–C₆alkyl, R₆ is C₁–C₆alkyl, and R₇ is C₁–C₆alkoxy, or R₆ and R₇ together are tetramethylene, pentamethylene, 3-oxa-1,5-pentylene or —CH₂CH₂O—C(O)— optionally substituted with C₁–C₄alkyl, phenyl or benzyl, and Z is Cl, Br or I.

10. A compound according to claim 2, that corresponds to formula IIa

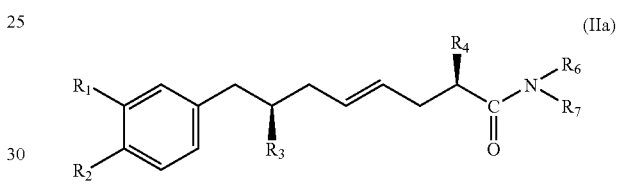

(IIa)

wherein R₁ and R₂ are independently of one another H, C₁–C₆alkyl, C₁–C₆halogenalkyl, C₁–C₆alkoxy, C₁–C₆alkoxy-C₁–C₆alkyl, or C₁–C₆alkoxy-C₁–C₆alkyloxy, R₃ is C₁–C₆alkyl, R₄ is C₁–C₆alkyl, R₆ is C₁–C₆alkyl, and R₇ is C₁–C₆alkyl or C₁–C₆alkoxy, or R₆ and R₇ together are tetramethylene, pentamethylene, 3-oxa-1,5-pentylene or —CH₂CH₂O—C(O)— optionally substituted with C₁–C₄alkyl, phenyl or benzyl.

* * * * *